(12) United States Patent
Arias

(10) Patent No.: US 9,250,227 B2
(45) Date of Patent: *Feb. 2, 2016

(54) SYSTEM AND METHOD FOR DETERMINING A TIME WHEN THE BLOOD ALCOHOL CONCENTRATION HAS PASSED A THRESHOLD LEVEL

(75) Inventor: Miguel Arias, Hagersten (SE)

(73) Assignee: Alco Systems Sweden AB, Stockholm (SE)

( * ) Notice: Subject to any disclaimer, the term of this patent is extended or adjusted under 35 U.S.C. 154(b) by 894 days.

This patent is subject to a terminal disclaimer.

(21) Appl. No.: 12/095,358

(22) PCT Filed: Nov. 29, 2006

(86) PCT No.: PCT/SE2006/050521
§ 371 (c)(1),
(2), (4) Date: May 29, 2008

(87) PCT Pub. No.: WO2007/064295
PCT Pub. Date: Jun. 7, 2007

(65) Prior Publication Data
US 2008/0294059 A1   Nov. 27, 2008

(30) Foreign Application Priority Data
Nov. 29, 2005   (SE) ........................ 0502615

(51) Int. Cl.
*G01N 33/497* (2006.01)
(52) U.S. Cl.
CPC ................. *G01N 33/4972* (2013.01)
(58) Field of Classification Search
None
See application file for complete search history.

(56) References Cited

U.S. PATENT DOCUMENTS

| | | | |
|---|---|---|---|
| 4,749,553 A * | 6/1988 | Lopez et al. | 422/84 |
| 5,157,601 A | 10/1992 | Jones et al. | |
| 5,783,449 A | 7/1998 | Kuznetsov | |
| 6,075,444 A | 6/2000 | Sohège et al. | |
| 6,594,482 B1 * | 7/2003 | Findikli et al. | 455/411 |
| 6,608,399 B2 * | 8/2003 | McConnell et al. | 307/10.1 |
| 6,697,732 B1 * | 2/2004 | Gotfried | 701/516 |
| 8,381,573 B2 | 2/2013 | Keays | |
| 2002/0127145 A1 * | 9/2002 | Der Ghazarian et al. | 422/83 |
| 2005/0053523 A1 * | 3/2005 | Brooke | 422/68.1 |

FOREIGN PATENT DOCUMENTS

| | | |
|---|---|---|
| DE | 10023148 A1 | 11/2001 |
| FR | 2687490 A1 * | 8/1993 |
| WO | WO 02/12883 A1 | 2/2002 |
| WO | 03079009 A1 | 9/2003 |
| WO | WO 03/079009 A1 | 9/2003 |
| WO | WO 2006026741 A1 * | 3/2006 |

OTHER PUBLICATIONS

Rockerbie et al. Computer simulation analysis of blood alcohol. Journal of Clinical Forensic Medicine, vol. 2, pp. 137-141, 1995.*
Watson et al. Prediction of blood alcohol concentration in human subjects. Journal of Studies on Alcohol, vol. 42, No. 7, pp. 547-556, 1981.*
Ramchandani et al. Research advances in ethanol metabolism. Pathologie Biologie, vol. 49, No. 9, pp. 676-682, 2001.*
Dec. 28, 2011 Search Report issued in European Patent Application No. 06824590.1.
Winter, Martin, et al., "What Are Batteries, Fuel Cells, and Supercapacitors?"; Chem Rev. 2004, 104, pp. 4245-4269.
Statement from US Licensee (Rightback Corp.) regarding Alcosystems Product IBAC, electronically dated Aug. 10, 2013.

* cited by examiner

*Primary Examiner* — Jennifer Dunston
(74) *Attorney, Agent, or Firm* — Baker & Hostetler LLP

(57) ABSTRACT

A system operable to determine a future point of time, at which the alcohol concentration in blood of a user is less than a threshold value. The system includes an alcohol sensor operable to detect a current alcohol concentration in blood of the user, and a portable apparatus. The alcohol sensor and the portable apparatus comprises each a wireless communication apparatus. The wireless communication apparatus in the alcohol sensor is operable to wirelessly transmit the current alcohol concentration to the wireless communication apparatus in the portable apparatus.

14 Claims, 3 Drawing Sheets

SYSTEM AND METHOD FOR DETERMINING A TIME WHEN THE BLOOD ALCOHOL CONCENTRATION HAS PASSED A THRESHOLD LEVEL

TECHNICAL FIELD OF THE INVENTION

The present invention relates in a first aspect to a system operable to determine a future point of time, at which the alcohol concentration in blood of a user is less than a threshold value.

In a second aspect the present invention relates to a method for determining a future point of time, at which the alcohol concentration in blood of a user is less than a threshold value.

In a third aspect the present invention relates to at least one computer program product for determining a future point of time, at which the alcohol concentration in blood of a user is less than a threshold value.

DESCRIPTION OF RELATED ART

The patent document U.S. Pat. No. 5,157,601 discloses an alcohol body concentration calculator 10 which will enable a drinker satisfactorily limit his body alcohol concentration. The alcohol body concentration calculator 10 comprises a keyboard 12, a buzzer of alarm 13, a four digit numerical display 14, a three digit numerical display 15, and a dot matrix display 16. The keyboard 12 incorporates a number of groups of keys: a numeric group generally indicated at 17, personal body characteristic keys generally indicated at 18, consumption keys generally indicated at 19, alarm control keys generally indicated at 20, a clock control key 21, and data identification and request keys generally indicated at 22. Having set the calculator 10 for his personal use, by using the keys 18, the user then sets the clock to the correct time. The user then carries the calculator 10 with him and when he is about to consume either food or alcohol he presses the respective one of consumption buttons 19 (food button 28 and alcohol button 29) and types in the starting time of the intake. It will be noted that the user is required to input information concerning the number of drinks or drink units that he has consumed. In order for this calculator 10 to work with high accuracy, a table is supplied with the device to assist the user in inserting the correct number of drink units.

A disadvantage with this calculator 10 is that it will probably not give a high accuracy as the user is getting more and more drunk, because he has to use and read a table and then input the correct number of drink units on the calculator 10. Another disadvantage is that it is a rather big calculator and that it has to be carried by the user all the time he is consuming food or alcohol.

The patent document U.S. Pat. No. 5,783,449 relates to an innovative Index-K which is used to help in diagnosing an alcohol disorder in human by taking into account individual differences in Alcohol Breakdown Activity (ABA). Using the Index-K instrument, a variety of pharmacokinetical data is integrated into a single value which is defined as the ratio between descending Area Under a plotted Curve (AUC) and the ascending AUC for a pharmacokinetical curve. This ratio presents the individual's quantitative assessment of the efficiency of ABA over displaying commensurability of the alcohol elimination power by virtue of the protection barriers for alcohol absorption. This method can be used as a diagnostic tool for alcoholism.

A disadvantage with this method is that it is not convenient for an unskilled user. This method is conveniently used by the health service in diagnosing alcoholism.

SUMMARY OF THE INVENTION

It is an object of the present invention to solve the above mentioned problem. It is also an object of the invention to provide a very convenient way for a user to determine a future point of time, at which the alcohol concentration in blood of the user is less than a threshold value.

According to the present invention there is provided in a first aspect a system operable to determine a future point of time, at which the alcohol concentration in blood of a user is less than a threshold value. The system comprises an alcohol sensor means operable to detect a current alcohol concentration in blood of the user, and a portable apparatus. The alcohol sensor means and the portable apparatus comprises each a wireless communication means. The wireless communication means in the alcohol sensor means is operable to wireless transmit the current alcohol concentration to the wireless communication means in the portable apparatus. The portable apparatus comprises also a to the wireless communication means connected control means, a clock means, and a memory means, each connected to the control means. The control means is operable to store the current alcohol concentration and a current time stamp from the clock means in the memory means. The portable apparatus comprises also a to the control means connected calculation means operable to calculate the future point of time in dependence of a known alcohol burn rate of the user stored in the memory means, or an alcohol burn rate calculated by the calculation means in dependence of characteristics of the user which have an influence on the alcohol burn rate.

An advantage with this system is that the user only has to handle the alcohol sensor means when he/she is consuming alcohol. This will probably increase the accuracy because the user will not have to read a table and then input the correct number of drink units on e.g. a calculator. Another important advantage with this system is that it is very convenient for an unskilled user to use. Furthermore, the system is also very flexible.

A further advantage in this context is achieved if said portable apparatus also comprises said control means connected to an input means with the aid of which said user is able to input said characteristics of said user in the form of sex, age, weight, health status, pregancy, kidneys, stomach, diet, physical fitness, diseases that affect said alcohol burn rate, and any drugs that said user takes.

Furthermore, it is an advantage in this context if said alcohol sensor means also comprises a means operable to receive exhalation air from said user, and in that said alcohol sensor means comprises a fuel-cell.

A further advantage in this context is achieved if said wireless communication means each is a radio transmitting and receiving device using low power.

Furthermore, it is an advantage in this context if portable apparatus is in the form of a mobile telephone, a mobile communicator, a personal digital assistant, a handheld computer, a navigation equipment, or a portable computer.

A further advantage in this context is achieved if the portable apparatus can be connected to an ignition unit of a motor vehicle, whereby said vehicle is prevented from getting started if the current alcohol concentration is higher than a predetermined threshold value.

Another object of the invention is to provide a method for determining a future point of time, at which the alcohol concentration in blood of a user is less than a threshold value. The method comprises the following steps:

to detect a current alcohol concentration in blood of said user with the aid of an alcohol sensor means;
   to wireless transmit said current alcohol concentration to a portable apparatus; and
   to calculate said future point of time in dependence of a known alcohol burn rate of said user, or an alcohol burn rate calculated in dependence of characteristics of said user which have an influence on said alcohol burn rate.

An advantage with this method is that the user only has to handle the alcohol sensor means when he/she is consuming alcohol. This will probably increase the accuracy because the user will not have to read any table and then input the correct number of drink units on e.g. a calculator. Another important advantage with this method is that it is very convenient for an unskilled user to use. Furthermore, the method is also very flexible.

A further advantage in this context is achieved if said method also comprises the step:

to input said characteristics of said user in the form of sex, age, weight, health status, pregnancy, kidneys, stomach, diet, physical fitness, diseases that affect said alcohol burn rate, and any drugs that said user takes.

Furthermore, it is an advantage in this context if said method also comprises the step:

that said user exhales exhalation air into said alcohol sensor means, and in that said alcohol sensor means comprises a fuel-cell.

A further advantage in this context is achieved if said wireless transmission step is performed with the aid of a radio transmitting and receiving device using low power.

Furthermore, it is an advantage in this context if said portable apparatus is in the form of a mobile telephone, a mobile communicator, a personal digital assistant, a handheld computer, a navigation equipment, or a portable computer.

A further advantage in this context is achieved if said method also comprises the steps:

to connect said portable apparatus to an ignition unit of a motor vehicle; and
   to prevent said motor vehicle from getting started if said current alcohol concentration is higher than a predetermined threshold value.

Another object of the invention is to provide at least one computer program product directly loadable into the internal memory of at least one digital computer. The at least one computer program product comprises software code portions for performing the steps of the method according to the present invention, when the at least one product/products is/are run on the at least one computer.

An advantage with this/these computer program product/products is/are that the user only has to handle the alcohol sensor means when he/she is consuming alcohol. This will probably increase the accuracy because the user will not have to read any table and then input the correct number of drink units on e.g. a calculator. Another important advantage with this/these product/products is/are that it/they is/are very convenient for an unskilled user to use. Furthermore, the product/products is/are very flexible.

It should be emphasized that he term "comprises/comprising" when used in this specification is taken to specify the presence of stated features, steps or components but does not preclude the presence of one or more other features, integers, steps, components or groups thereof.

Embodiments of the invention will now be described with a reference to the accompanying drawings, in which:

DETAILED DESCRIPTION OF EMBODIMENTS

Figure 1:
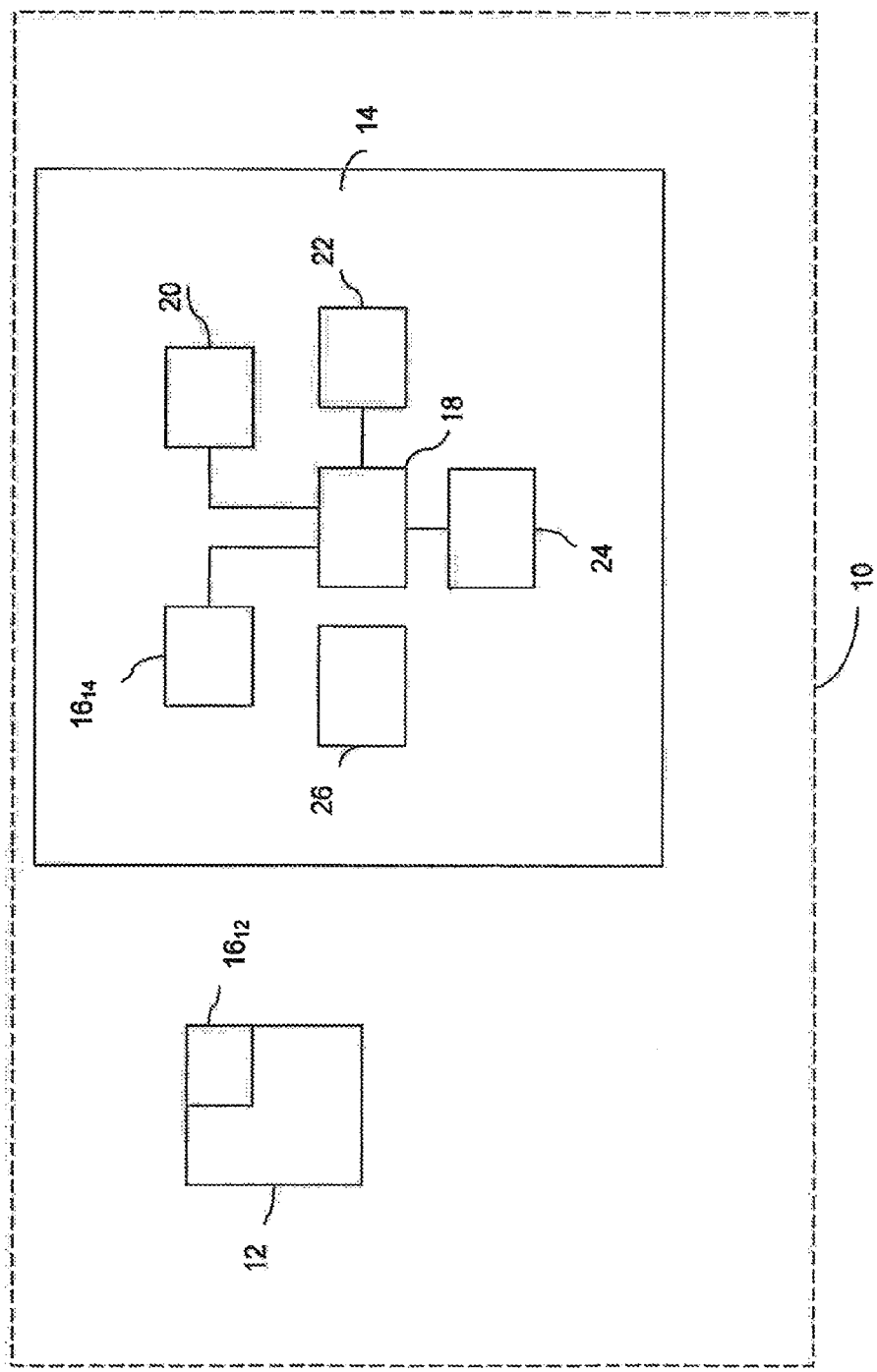
FIG. 1 shows a block diagram of a system operable to determine a future point of time, at which the alcohol concentration in blood of a user is less than a threshold value according to the present invention.

In FIG. 1 there is disclosed a system 10 operable to determine a future point of time, at which the alcohol concentration in blood of a user is less than a threshold value according to the present invention. The system 10 comprises an alcohol sensor means 12 operable to detect a current alcohol concentration in blood of the user. As also is apparent in FIG. 1, the system 10 also comprises a portable apparatus 14. The alcohol sensor means 12 and the portable apparatus 14 each comprises a wireless communication means $16_{12}$; $16_{14}$. The wireless communication means $16_{12}$ in the alcohol sensor means 12 is operable to wirelessly 5 transmit the current alcohol concentration to the wireless communication means $16_{14}$ in the portable apparatus 14. As is apparent in FIG. 1, the portable apparatus 14 also comprises the wireless communication means $16_{14}$ connected control means 18, a clock means 20, and a memory means 22, each connected to the control means 18. The control means 18 is operable to store the current alcohol concentration and a current time stamp from the clock means 20 in the memory means 22. The portable apparatus 14 also comprises a to the control means 18 connected calculation means 24 operable to calculate the future point of time in dependence of a known alcohol burn rate of the user stored in the memory means 22, or an alcohol burn rate calculated by the calculation means 24 in dependence of characteristics of the user which have an influence on the alcohol burn rate. As also is apparent in FIG. 1, the portable apparatus 14 can also comprise an input means 26 connected to the control means 18. With the input means 26, e.g. a keypad, the user is able to input the characteristics of the user in the form of sex, age, weight, health status, pregnancy, kidneys, stomach, diet, physical fitness, diseases that affect the alcohol burn rate, and any drugs that the user takes.

According to one preferred embodiment of the system 10, the alcohol sensor means 12 also comprises a means (not disclosed) operable to receive exhalation air from the user. The alcohol sensor means 12 comprises in this embodiment a fuel-cell.

According to another embodiment of the system 10, each of the wireless communication means $16_{12}$; $16_{14}$ is a radio transmitting and receiving device using low power such as Bluetooth®.

According to yet another preferred embodiment of the system 10, the portable apparatus 14 is in the form of a mobile telephone, a mobile communicator, a personal digital assistant, a handheld computer, a navigation equipment, or a portable computer.

According to another preferred embodiment of the system 10, the portable apparatus 14 can be connected to an ignition unit of a motor vehicle, whereby the motor vehicle is prevented from getting started if the current alcohol concentration is higher than a predetermined value.

Figure 2:
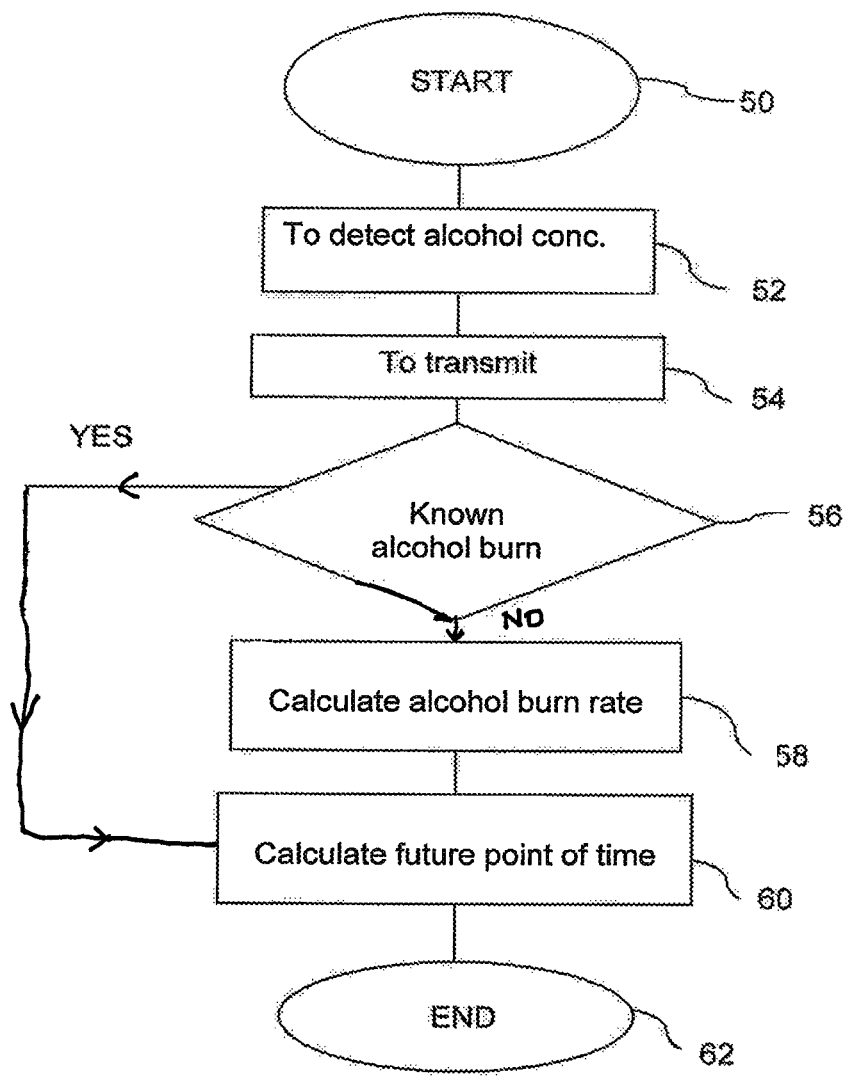
FIG. 2 is a flow chart of a method for determining a future point of time, at which the alcohol concentration in blood of a user is less than a threshold value according to the present invention.

In FIG. 2 there is disclosed a flow chart of a method for determining a future point of time, at which the alcohol concentration in blood of a user is less than a threshold value according to the present invention. The method begins at block 50. At block 52 the method continues with the step: to detect a current alcohol concentration in blood of the user with the aid of an alcohol sensor means 12 (see FIG. 1). Thereafter, the method continues, at block 54, with the step: to wireless transmit the current alcohol concentration from the alcohol sensor means 12 to a portable apparatus 14 (see FIG. 1). The method then continues, at block 56, to ask the question: Is there a known alcohol burn rate for the user? If the answer to this question is affirmative, the method continues, at block 60, with the step: to calculate the future point of time in dependence of the known alcohol burn rate of the user. On the other, if the if the answer to the question is negative, the method continues, at block 58, with the step: to calculate an alcohol burn rate for the user in dependence of characteristics of the user which have an influence on the alcohol burn rate. Thereafter, the method continues, at block 60, with the step: to calculate the future point of time in dependence of the calculated alcohol burn rate. The method is competed at block 62.

According to another preferred embodiment of the method according to the present invention, the method also comprises the step: to input the characteristics of the user in the form of sex, age, weight, health status, pregnancy, kidneys, stomach, diet, physical fitness, diseases that affect the alcohol burn rate, and any drugs taken by the user.

According to yet another embodiment of the method according to the present invention, the method also comprises the step performed by the user: to exhale exhalation air into the alcohol sensor means 12. According to this embodiment, the alcohol sensor means 12 comprises a fuel-cell.

According to another preferred embodiment of the method according to the present invention, the wireless transmission step is performed with the aid of a radio transmitting and receiving device using low power such as Bluetooth®.

According to yet another embodiment of the method, the portable apparatus 14 is in the form of a mobile telephone, a mobile communicator, a personal digital assistant, a handheld computer, a navigation equipment, or a portable computer.

According to another preferred embodiment of the method according to the present invention, the method also comprises the steps: to connect the portable apparatus 14 to an ignition unit of a motor vehicle; and to prevent the motor vehicle from getting started if the current alcohol concentration of the user is higher than a predetermined threshold value.

Figure 3:
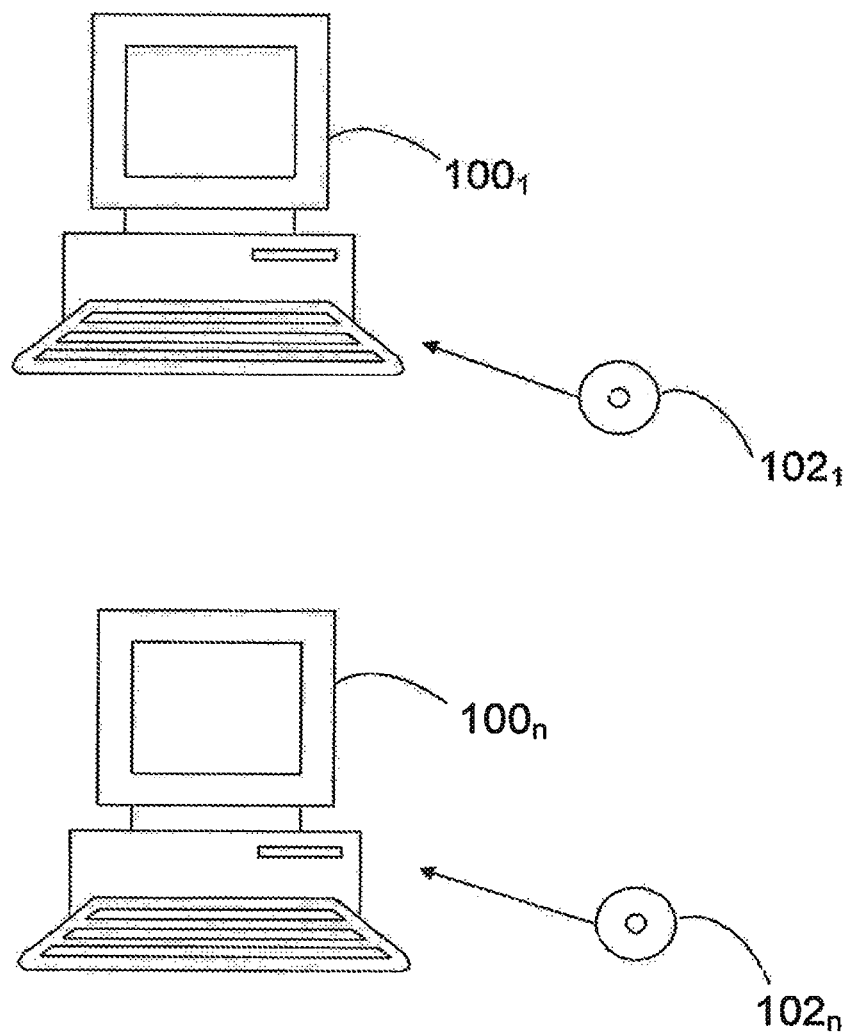
FIG. 3 shows a schematic diagram of some computer program products according to the present invention.

In FIG. 3 there is disclosed a schematic diagram of some computer program products according to the present invention. There is disclosed n different digital computers $100_1, \ldots, 100_n$, wherein n is an integer. There is also disclosed n different computer program products $102_1, \ldots, 102_n$, here showed in the form of compact discs. The different computer program products $102_1, \ldots, 102_n$ are directly loadable into the internal memory of the n different digital computers $100_1, \ldots, 100_n$. Each computer program product $102_1, \ldots, 102_n$ comprises software code portions for performing some or all the steps of FIG. 2 when the product(s) $102_1, \ldots, 102_n$ is/are run on said computer(s) $100_1, \ldots, 100_n$. Said computer program products $102_1, \ldots, 102_n$ can e.g. be in the form of floppy disks, RAM disks, magnetic tapes, opto magnetical disks or any other suitable products.

It is pointed out that the calculation means 24 (see FIG. 1) make use of formulas about the burn rate of alcohol in the human body. The formulas are parameterized to allow for individual forecasting of when the person/user can start driving cars, start to breast-feed etc.

The system 10 can also be calibrated to enhance the reading accuracy. The calibration can be done over many different occasions or during the same occasion.

Due to the use of the characteristics of the user, the system 10 can be what is called a self calibrating system 10.

Due to the use of the clock means 20 in the system 10, the system 10 makes use of a so called time axle in that the clock means 20 keeps record of the current time and the system 10 performs corrections dependent on e.g. the aging of the user.

It is pointed out that the portable apparatus 14 can be used in cars, boats or any other type of vehicles.

The system 10 can also be used to check employees before they are entitled to proceed with their duties, e.g. to check-out keys to busses, taxis, trucks etc. It can also be used as a combined time clock and safety device.

The invention is not limited to the embodiments described in the foregoing. It will be obvious that many different modifications are possible within the scope of the following claims.

The invention claimed is:

1. A system operable to determine a future point of time when a user can operate a vehicle, at which the alcohol concentration in blood of a user is less than a threshold value, the system comprises an alcohol sensor operable to detect a current alcohol concentration in blood of the user, and a portable apparatus,
    wherein the alcohol sensor, and the portable apparatus each independently comprise a wireless communication device, wherein a first wireless communication device in the alcohol sensor is operable to wirelessly transmit the current alcohol concentration to a second wireless communication device in the portable apparatus, and
    wherein the portable apparatus further comprises a controller, a clock, and a memory, wherein the controller is connected to the second wireless communication device, the clock, and the memory, and the controller is operable to store the current alcohol concentration and a time stamp from the clock in the memory, and
    wherein the controller is connected to a calculation device operable to calculate the future point of time in dependence of the current alcohol concentration detected by the alcohol sensor and of a known alcohol burn rate of the user stored in the memory means, or an alcohol burn rate calculated by the calculation means in dependence of characteristics of the user which have an influence on the alcohol burn rate, wherein said characteristics of the user are selected from the group consisting of sex and weight and combinations thereof, and
    wherein the alcohol sensor further comprises a device configured to receive exhalation air from the user, and a fuel cell, and
    wherein the calculation device is operable to be self-calibrated during use through software comprising formulas that are parameterized to the user.

2. A system operable to determine a future point of time when a user can operate a vehicle, at which the alcohol concentration in blood of a user is less than a threshold value according to claim 1, wherein the controller is further connected to an input with the aid of which the user is able to input the characteristics, wherein the characteristics comprise sex and weight.

3. A system operable to determine a future point of time when a user can operate a vehicle, at which the alcohol concentration in blood of a user is less than a threshold value according to claim 1, wherein the first and second wireless communication device independently comprise a radio transmitting and receiving device.

4. A system operable to determine a future point of time when a user can operate a vehicle, at which the alcohol concentration in blood of a user is less than a threshold value according to claim 1, wherein the portable apparatus is a mobile telephone, a mobile computer, a personal digital assistant, a handheld computer, a navigation equipment, or a portable computer.

5. A system operable to determine a future point of time when a user can operate a vehicle, at which the alcohol concentration in blood of a user is less than a threshold value according to claim 1, wherein the portable apparatus can be connected to an ignition unit of a motor vehicle, whereby the vehicle is prevented from getting started if the current alcohol concentration is higher than a predetermined threshold value.

6. A system operable to determine a future point of time when a user can operate a vehicle, at which the alcohol concentration in blood of a user is less than a threshold value according to claim 1, wherein the portable apparatus is configured to be carried and transported by a user and is configured with its own power source so as to be operated independent of an external power source.

7. A system operable to determine a future point of time when a user can operate a vehicle, at which the alcohol concentration in blood of a user is less than a threshold value according to claim 1, wherein the calculation device is configured to calculate the future point of time in dependence of a known alcohol burn rate of the user stored in the memory.

8. A system operable to determine a future point of time when a user can operate a vehicle, at which the alcohol concentration in blood of a user is less than a threshold value according to claim 1, wherein the alcohol sensor is configured to communicate with the portable apparatus to cause the portable apparatus to automatically re-transmit the blood alcohol concentration to interested parties or external devices with no interference by the user.

9. A method for determining a future point of time when a user can operate a vehicle, at which the alcohol concentration in blood of a user is less than a threshold value, the method comprising the steps of:
  (a) having a user exhale exhalation air into an alcohol sensor comprising a fuel cell;
  (b) detecting a current alcohol concentration in blood of the user with the alcohol sensor;
  (c) wirelessly transmitting the current alcohol concentration to a portable apparatus comprising a calculation device;
  (d) inputting characteristics of the user, which have an influence on the alcohol burn rate selected from the group consisting of sex and weight and combinations thereof, using the portable apparatus; and
  (e) using:
    (1) the wirelessly-transmitted current alcohol concentration, and
    (2) a software that makes use of either;
      (i) a known alcohol burn rate of the user, or
      (ii) an alcohol burn rate calculated through use of said software based on characteristics of the user from step (d), which have an influence on the alcohol burn rate,
  to calculate the future point of time;
  said method further comprising self-calibrating the calculation device during the method through use of said software; wherein said software comprises formulas that are parameterized to the user.

10. A method for determining a future point of time when a user can operate a vehicle, at which the alcohol concentration in blood of a user is less than a threshold value according to claim 9, wherein the wireless transmission step is performed with a radio transmitting and receiving step.

11. A method for determining a future point of time when a user can operate a vehicle, at which the alcohol concentration in blood of a user is less than a threshold value according to claim 9, wherein the portable apparatus is a mobile telephone, a mobile computer, a personal digital assistant, a handheld computer, a navigation equipment, or a portable computer.

12. A method for determining a future point of time when a user can operate a vehicle, at which the alcohol concentration in blood of a user is less than a threshold value according to claim 9, the method further comprises the following steps:
  (f) connecting the portable apparatus to an ignition unit of a motor vehicle; and
  (g) preventing the motor vehicle from getting started if the current alcohol concentration is higher than a predetermined threshold value.

13. A method for determining a future point of time when a user can operate a vehicle, at which the alcohol concentration in blood of a user is less than a threshold value according to claim 9, wherein the future point of time is calculated in dependence of known alcohol burn rate of a user stored in a memory.

14. A method for determining a future point of time when a user can operate a vehicle, at which the alcohol concentration in blood of user is less than a threshold value according to claim 9, wherein the alcohol sensor communicates with the portable apparatus and then causes the portable apparatus to automatically re-transmit the blood alcohol concentration to interested parties or external devices with no interference by the user.

* * * * *